(12) United States Patent
Jansen et al.

(10) Patent No.: US 10,793,501 B2
(45) Date of Patent: Oct. 6, 2020

(54) METHOD FOR PROVIDING A SUCCINIC ACID SOLUTION

(71) Applicant: PURAC BIOCHEM B.V., Gorinchem (NL)

(72) Inventors: Peter Paul Jansen, Gorinchem (NL); Jan Van Breugel, Gorinchem (NL); Gerard Hendrik Van Bochove, Gorinchem (NL); Jose Maria Vidal Lancis, Gorinchem (NL); Tanja Dekic Zivkovic, Gorinchem (NL)

(73) Assignee: PURAC BIOCHEM B.V., Gorinchem (NL)

( * ) Notice: Subject to any disclaimer, the term of this patent is extended or adjusted under 35 U.S.C. 154(b) by 316 days.

(21) Appl. No.: 15/747,189

(22) PCT Filed: Jul. 29, 2016

(86) PCT No.: PCT/EP2016/068169
§ 371 (c)(1),
(2) Date: Jan. 24, 2018

(87) PCT Pub. No.: WO2017/021303
PCT Pub. Date: Feb. 9, 2017

(65) Prior Publication Data
US 2018/0208534 A1    Jul. 26, 2018

(30) Foreign Application Priority Data

Jul. 31, 2015 (EP) .................................... 15179272

(51) Int. Cl.
| | | |
|---|---|---|
| *C07C 51/41* | (2006.01) | |
| *C12P 7/46* | (2006.01) | |
| *C07C 51/43* | (2006.01) | |
| *C01B 7/03* | (2006.01) | |
| *C01F 5/30* | (2006.01) | |
| *C01F 5/10* | (2006.01) | |
| *C07C 51/02* | (2006.01) | |
| *C01F 5/06* | (2006.01) | |

(52) U.S. Cl.
CPC .............. *C07C 51/43* (2013.01); *C01B 7/035* (2013.01); *C01F 5/06* (2013.01); *C01F 5/10* (2013.01); *C01F 5/30* (2013.01); *C07C 51/02* (2013.01); *C07C 51/412* (2013.01); *C12P 7/46* (2013.01)

(58) Field of Classification Search
CPC ....... C07C 55/10; C07C 51/53; C07C 51/412; C01B 7/035; C01F 5/06; C01F 5/10; C01F 5/30; C12P 7/46
See application file for complete search history.

(56) References Cited

U.S. PATENT DOCUMENTS

| | | |
|---|---|---|
| 2014/0200365 A1 | 7/2014 | De Haan et al. |
| 2015/0044741 A1 | 2/2015 | Cerda Baro et al. |

FOREIGN PATENT DOCUMENTS

| | | |
|---|---|---|
| CN | 101550079 A | 10/2009 |
| JP | 2014524254 A | 9/2014 |
| JP | 2015508758 A | 3/2015 |
| WO | 2013/025105 A1 | 2/2013 |
| WO | 2013/117687 A1 | 8/2013 |
| WO | 2015/000956 A1 | 1/2015 |
| WO | 2015/150325 A1 | 10/2015 |

OTHER PUBLICATIONS

Machine translation of CN 101550079A (published May 12, 2009) downloaded from the EPO on Jan. 31, 2020. (Year: 2009).*
Kholer et al. Ind. Eng. Chem. Res. (1987) 26: 652-656 (Year: 1987).*
International Search Report and Written Opinion in International Application No. PCT/EP2016/068169, dated Oct. 6, 2016.

* cited by examiner

*Primary Examiner* — Susan M Hanley
(74) *Attorney, Agent, or Firm* — J.A. Lindeman & Co. PLLC

(57) ABSTRACT

The invention pertains to a method for providing a succinic acid solution, comprising the steps of —providing a first magnesium succinate containing medium with a magnesium succinate concentration of 18-23 wt. % to a first acidification reactor where it is contacted with hydrogen chloride to form a solution of succinic acid, magnesium chloride and hydrogen chloride, —providing a second magnesium succinate containing medium with a magnesium succinate concentration of 25-50 wt. %, and contacting it in a second acidification reactor with the solution of succinic acid, magnesium chloride and hydrogen chloride withdrawn from the first acidification reactor, to form an aqueous mixture comprising magnesium chloride and succinic acid with a succinic acid concentration of at least 18 wt. %. The method according to the invention makes it possible to obtain a solution comprising succinic acid and magnesium 20 chloride with an increased succinic acid concentration.

10 Claims, 4 Drawing Sheets

METHOD FOR PROVIDING A SUCCINIC ACID SOLUTION

Figure 1:
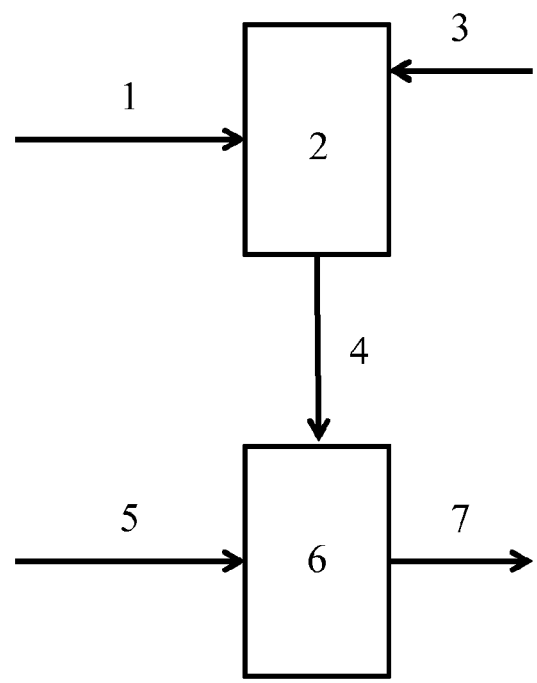

The invention pertains to a method for providing a succinic acid solution.

Succinic acid, also known as butanedioic acid, has many industrial applications. It is used, e.g., in the food and beverage industry. It is also used as a starting material for the production of succinate esters, which can e.g., be used as starting material for the production of butane diol, which in turn can be used as monomer in the manufacture of plastics.

An attractive way to manufacture succinic acid is through a fermentation process, wherein a carbon source is fermented by means of a microorganism to form succinic acid. The liquid wherein the carbohydrate source is fermented is called the fermentation broth or the fermentation medium. The formation of succinic acid during fermentation will result in a decrease of the pH of the fermentation broth. Since such a decrease in pH can damage the microorganism's metabolic process, it is common practice to add a neutralizing agent, i.e. a base, to the fermentation medium, to keep the pH in a range where the microorganism can perform. As a result, the succinic acid produced will be present in the fermentation medium in the form of a succinate salt, with the cation of the salt being the cation of the base added during fermentation.

To recover the succinic acid from the fermentation broth after fermentation, downstream processing is required. In such processing, the succinate salt in the fermentation broth needs to be converted into succinic acid. Also, the succinic acid (or succinate if not yet converted) needs to be isolated from the fermentation broth. Since a fermentation broth comprises many compounds, including significant amounts of biomass (such as microorganisms) and salt (originating from the neutralizing agent), recovering and isolating succinic acid can be rather complex.

WO 2013/025105 A1 describes a method for preparing succinic acid, which method comprises the steps of providing magnesium succinate, in particular though a fermentation process, acidifying the magnesium succinate with hydrochloric acid to obtain a solution comprising succinic acid and magnesium chloride, concentrating the solution comprising succinic acid and magnesium chloride, and precipitating succinic acid from the solution. The magnesium chloride solution may be subjected to a thermal decomposition step to form hydrogen chloride and magnesium oxide.

While the method as described in this reference is quite attractive, there is still need for further improvement. In particular, it has been found that the succinic acid yield of the process needs to be improved.

CN 101 550 079 A discloses a process for the purification of succinic acid in which an aqueous succinate solution is neutralized in three subsequent steps performed in three separate neutralization reactors, wherein in each step a concentrated aqueous hydrochloric acid solution is added to gradually neutralize the succinate. The disadvantage of this process, however, can be seen in the fact that, as an aqueous hydrochloric acid solution is used for neutralization, in each of the three neutralization steps water is introduced into the succinate solution which at least partially has to be removed again before crystallization in order to ensure that a sufficient amount of succinic acid is precipitated in the form of crystals. As the aqueous solution obtained after acidification is corrosive, problems often occur if water is removed from such acidic solutions by means of evaporation. A further disadvantage of the process disclosed in CN 101 550 079 A is that yield is only about 70%, wherein this value has been calculated on the basis of the data given in the Examples of this prior art document. Such low yields, however, are too low for an economically feasible process.

The present invention provides a method for providing a succinic acid solution which solves this problem.

The invention pertains to a method for providing a succinic acid solution, comprising the steps of
  providing a first magnesium succinate containing medium with a magnesium succinate concentration of 18-23 wt. % to a first acidification reactor where it is contacted with hydrogen chloride to form a solution of succinic acid, magnesium chloride and hydrogen chloride,
  providing a second magnesium succinate containing medium with a magnesium succinate concentration of 25-50 wt. %, and contacting it in a second acidification reactor with the solution of succinic acid, magnesium chloride and hydrogen chloride withdrawn from the first acidification reactor, to form an aqueous mixture comprising magnesium chloride and succinic acid with a succinic acid concentration of at least 18 wt. %.

It has been found that the method according to the invention makes it possible to obtain a solution comprising succinic acid and magnesium chloride with an increased succinic acid concentration. This results in a higher succinic acid yield in a subsequent succinic acid precipitation step. It also results in less water in the magnesium chloride solution, which is attractive in the further processing of that solution. A further advantage is that water is evaporated from a solution which does not contain HCl. Because HCl is a corrosive compound, removal of water from a solution which does not contain this compound is attractive, as it places lower requirements on the apparatus used in the evaporation. Further advantages of the present invention and the specific embodiments thereof will become clear from the further specification.

The invention will be discussed in more detail below, with reference to the Figures, without being limited thereto or thereby.

FIG. 1 provides a representation of a first embodiment of the present invention.

Figure 2:
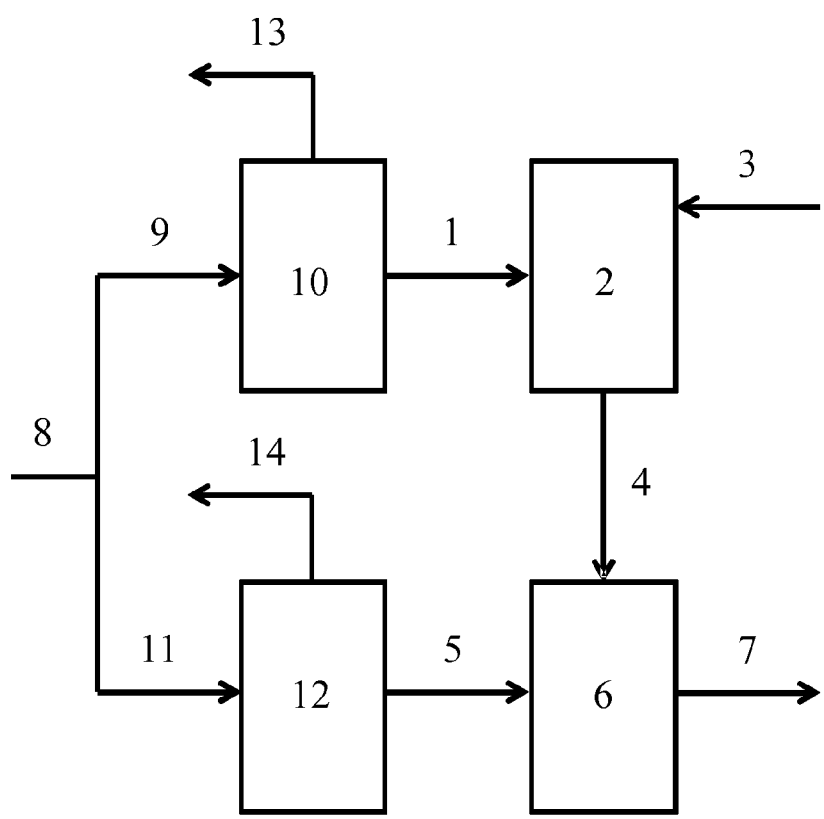

FIG. 2 provides a representation of a further embodiment of the present invention.

Figure 3:
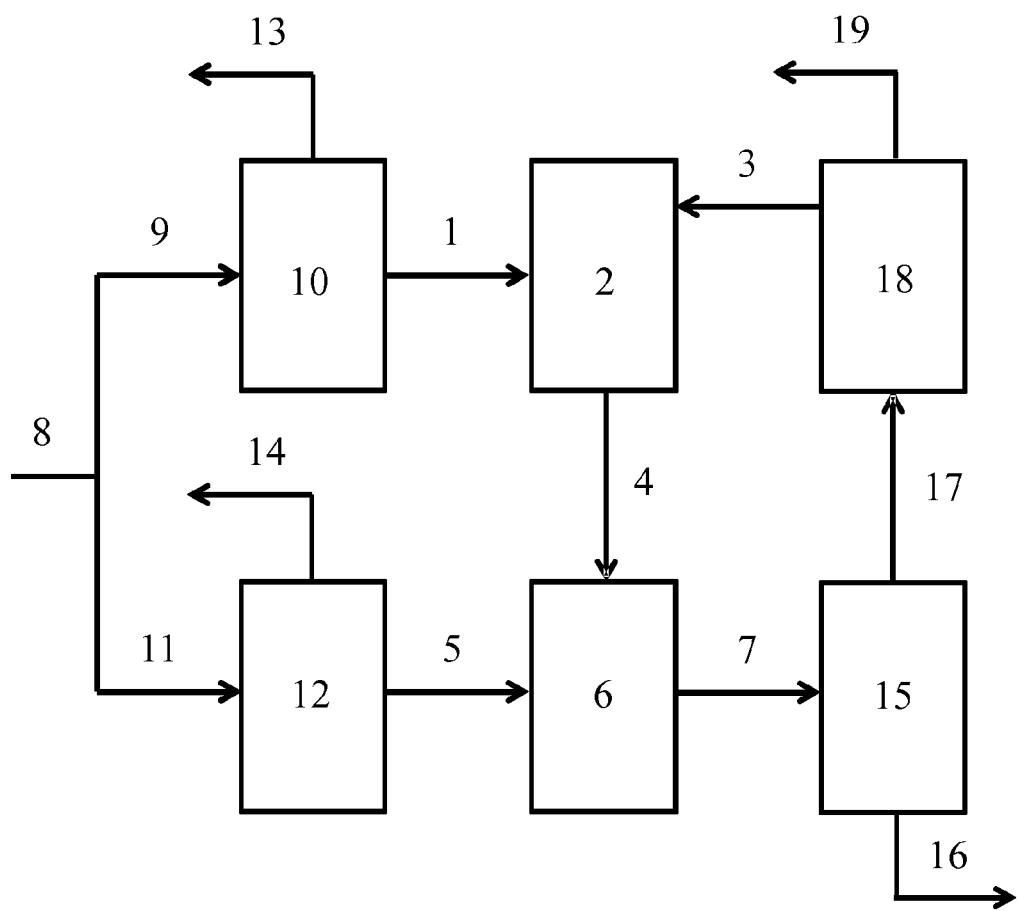

FIG. 3 provides a representation of a still further embodiment of the present invention.

Figure 4:
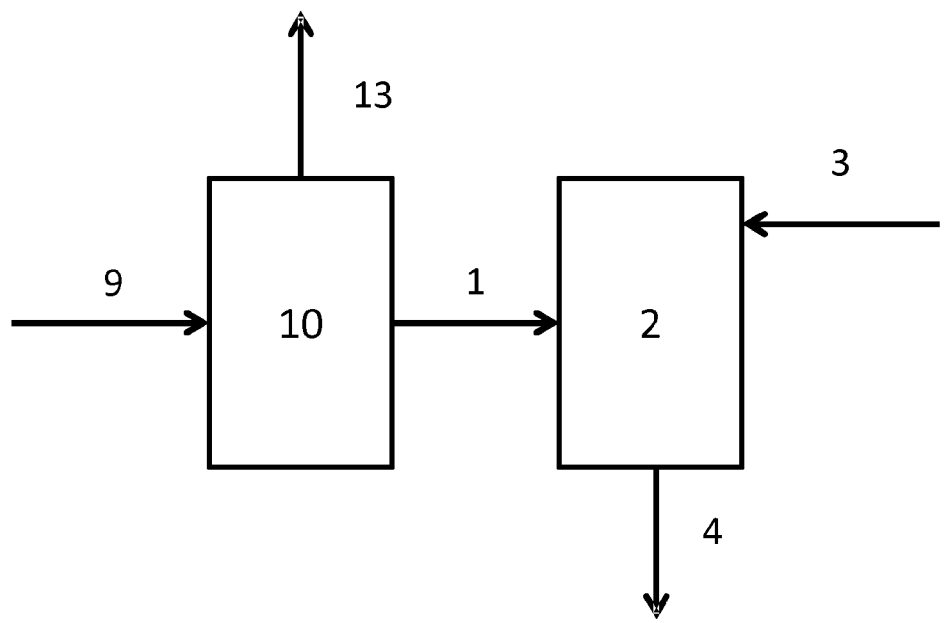

FIG. 4 provides a representation of a purification process pursuant to the teaching in WO 2013/025105 A1.

It is a feature of the present invention that two magnesium succinate containing media are used, namely a first magnesium succinate containing medium with a magnesium succinate concentration of 18-23 wt. %, and a second magnesium succinate containing medium with a magnesium succinate concentration of 25-50 wt. %. The first magnesium succinate containing medium generally is a magnesium succinate solution. It is acidified with HCl, to form a solution of succinic acid, magnesium chloride and excess hydrogen chloride, and this solution is then used to acidify the second magnesium succinate containing medium. Depending on the concentration, the second magnesium succinate containing medium can be a magnesium succinate solution. It can also be a slurry of magnesium succinate in a magnesium succinate solution.

In FIG. 1 a first aqueous magnesium succinate containing medium with a concentration in the range of 18-23 wt. % is provided through line (1) to a first acidification reactor (2). In the first acidification reactor (2), HCl is added through line (3), and an aqueous solution comprising succinic acid, magnesium chloride, and HCl is withdrawn through line (4), and provided to second acidification reactor (6). In second acidification reactor (6), it is combined with a second magnesium succinate containing medium with a magnesium succinate concentration of 25-50 wt. %, which is provided through line (5). This results in the formation of an aqueous mixture comprising magnesium chloride and succinic acid with a succinic acid concentration of at least 18 wt. %, which is withdrawn through line (7).

The first magnesium succinate containing medium has a magnesium succinate concentration in the range of 18-23 wt. %. Working at lower concentrations is possible, but generally not attractive because it will lead to the presence of unnecessarily high amounts of water in the system. The upper limit of the magnesium succinate concentration is governed by the concentration of succinic acid that will be formed in the first acidification reactor. If the amount of succinic acid formed here is too high, succinic acid will precipitate in the acidification reactor, and this may interfere with the acidification process.

The temperature and pressure of this solution are in principle not critical. It is generally appropriate to work at a pressure which is atmospheric, or slightly above or below atmospheric. A suitable pressure may, e.g., be in the range of 0.5-2 bar, in particular 0.9-1.2 bar. The temperature can, e.g., be in the range of 20-120° C. (wherein, when the temperature is above 100° C., the pressure will have to be selected at such a value that the solution is still in the liquid phase). However, temperatures at the higher end of the range are often preferred because at higher temperatures the solubility of magnesium succinate is increased. Further, the first magnesium succinate containing medium will often be derived from a step wherein water has been evaporated at increased temperature. This generally results in a higher temperature for the first magnesium succinate containing medium, e.g., in the range of 50-100° C., in particular 80-100° C.

In the first acidification reactor, the magnesium succinate solution is contacted with hydrogen chloride. HCl acidification may for example be conducted with an aqueous HCl solution or gaseous HCl. Where a HCl solution is used, it preferably has HCl concentration which is relatively high, to prevent the addition of unnecessary water to the system. The HCl solution therefore preferably comprises at least 5 wt. %, more preferably at least 10 wt. % and even more preferably at least 20 wt. % HCl.

The use of a gaseous HCl stream is also possible. In one embodiment the gaseous HCl stream is derived from the thermal decomposition of magnesium chloride. This will be discussed in more detail below. It has been found that the present invention is particularly attractive for processing gaseous HCl streams, in particular those which are derived from the thermal decomposition of magnesium chloride.

The amount of HCl added in the first acidification step is governed not only by the amount necessary to convert the amount of magnesium succinate in the first acidification step into succinic acid, but also by the amount of magnesium succinate that is to be converted into succinic acid in the second acidification step. It may be preferred that the ratio of the total amount of HCl provided to the process and the total amount of magnesium succinate provided to the process is such that there is a slight excess of HCl. For example, the excess of HCl used may be such that the final aqueous mixture comprising succinic acid and magnesium chloride has a pH 2 or lower, preferably a pH of 0-2, in particular a pH of 1-2.

The temperature of the HCl may vary within wide ranges, e.g., between 5 and 130° C., also dependent on whether the HCl is provided in gaseous form, or in the form of an aqueous solution. Higher temperatures may be preferred, because the acidification reaction preferably is carried out at a higher temperature. Further, if the HCl is derived from the thermal decomposition of magnesium chloride, as will be discussed in more detail below, it will of itself have a higher temperature. A suitable temperature for the HCl may be in the range of 50-120° C., in particular 70-120° C.

The first acidification step results in the formation of a solution of succinic acid, magnesium chloride, and hydrogen chloride. The amounts of succinic acid and magnesium chloride are dependent on the amount of magnesium succinate provided with the first magnesium succinate containing medium and the amount of water provided with the HCl. In general, the solution comprises 15-23 wt. % of succinic acid, preferably 17-20 wt. %. The solution generally comprises 10-20 wt. % of magnesium chloride, in particular 12-17 wt. %. The amount of HCl present in the solution generally is in the range of 0.1 to 6 wt. %.

The temperature in the acidification reactor and of the solution produced therein may very within wide ranges, e.g., between 20 and 100° C. The solution preferably is at or about atmospheric pressure, e.g., between 0.9 and 1.2 bar. It is preferred for the temperature to be at the higher end of the range, as this will prevent the untimely precipitation of succinic acid. It may therefore be preferred for the solution to be at a temperature of 60-100° C., in particular 80-100° C.

The solution comprising succinic acid, magnesium chloride and HCl is provided to the second acidification reactor, where it is combined with a second magnesium succinate containing medium with a magnesium succinate concentration of 25-50 wt. %. The lower limit of this range is governed by the desire to keep the amount of water in the system as low as possible. The upper limit is governed by processing considerations. It may be preferred for the magnesium succinate concentration to be in the range of 30-50 wt. %, preferably in the range of 35-45 wt. %.

To be able to manage the magnesium succinate solution at these high concentrations, it is preferred for the solution to have a temperature of at least 50° C., in particular at least 80° C., more in particular at least 100° C. As maximum, a temperature of 160° C. may be mentioned. A preferred range may be 105-140° C. As will be evident to the skilled person, the solution should be under a pressure which is sufficiently high to ensure that the magnesium chloride is in the liquid phase.

In the second acidification reaction, the solution comprising succinic acid, magnesium chloride and HCl and the second magnesium succinate containing medium are combined. The temperature in the second acidification reactor and the temperature of the mixture withdrawn therefrom is not critical. As a general range 20-100° C. may be mentioned. To limit the amount of succinic acid precipitating in the acidification reactor it may be preferred for the temperature to be in the higher end of the range, e.g., between 50 and 100° C., more in particular between 80 and 100° C.

If so desired, some additional HCl may be added to the second acidification reactor. However, for reasons of process economy it is preferred for the amount of additional HCl added to the second acidification reaction to be limited. In particular, it is preferred that of the HCl required to neutralize the magnesium succinate in the second magnesium succinate containing medium, at least 50% is provided by the product of the first acidification reaction, in particular at least 70%, more in particular at least 90%. According to a particularly preferred embodiment of the process according to the present invention less than 5 mol-%, more preferably less than 1 mol-% and even more preferably less than 0.1 mol-% of HCl are added to the mixture in the second acidification reactor that is obtained by contacting the second magnesium succinate containing medium with the solution withdrawn from the first acidification reactor, in each case based on the total molar amount of succinic acid and magnesium succinate in that mixture. According to an even more preferred embodiment of the process according to the present invention almost no HCl is added at all to that mixture (which means that almost 100% of the HCl used to neutralize the magnesium succinate is provided by the product of the first acidification reaction).

In the process according to the invention the ratio between the first magnesium succinate containing medium and the second magnesium succinate containing medium can best be quantified by the relative amounts of succinate provided by these streams to the succinate present in the succinic acid end product. In one embodiment, of the succinate in the succinic acid end product between 10 and 90% is derived from the first magnesium succinate containing medium, in particular between 25 and 90%, more in particular between 50 and 90%. The balance is provided by the succinate derived from the second succinate containing medium.

Where the HCl is provided to the first acidification step in gaseous form, it is preferred for the liquid volume in the first acidification step to be so large that all HCl provided to the medium is absorbed, to prevent venting of HCl. This can be ensured by selecting a suitable temperature and a suitable liquid volume for the magnesium succinate containing medium. It is within the scope of the skilled person to effect this.

The product of the second acidification reaction is an aqueous mixture comprising magnesium chloride and at least 18 wt. % of succinic acid. Depending on the temperature and the further composition the mixture may be a solution with magnesium chloride and succinic acid both being dissolved, or it may be a suspension, with part of the succinic acid being dissolved and part of the succinic acid being present in the form of solid particles. In principle it is also possible that part of the magnesium chloride form is present in the form of solid particles. However, due to the high solubility of magnesium chloride, this is less likely to occur. The aqueous mixture generally has a succinic acid concentration of 18-30 wt. %, more in particular 18-25 wt. %. Concentrations higher than 30 wt. % are difficult to obtain. For concentrations lower than 18 wt. %, the process is of decreased economic interest. The magnesium chloride concentration of the aqueous mixture generally in the range of 10-25 wt. %, more in particular 15-25 wt. %, dependent on the magnesium succinate concentrations in the previous solutions.

As indicated above, the mixture generally has a pH of below 2, in particular between 0 and 2, more in particular between 1 and 2.

In one embodiment of the present invention, the first magnesium succinate containing medium and/or the second magnesium succinate containing medium, preferably both the first magnesium succinate containing medium and the second magnesium succinate containing medium, are obtained by subjecting an aqueous magnesium succinate solution with a magnesium succinate concentration in the range of 5-15 wt. % to a concentration step in an evaporation reactor wherein water is evaporated to obtain a magnesium succinate solution with the specified concentration.

Therefore, in one embodiment a magnesium succinate solution with a concentration in the range of 5-15 wt. % is subjected to an evaporation step at elevated temperature and/or reduced pressure to evaporate water to obtain a magnesium succinate containing medium with a concentration of 18-23 wt. %. For further properties of this medium reference is made to what is stated above for the medium to be provided to the first acidification reactor. Evaporation at elevated temperature at a pressure which is such that precipitation of magnesium succinate is prevented may be preferred for reasons of process control.

In a further embodiment a magnesium succinate solution with a concentration in the range of 5-15 wt. % is subjected to an evaporation step at elevated temperature and/or reduced pressure to evaporate water to obtain a magnesium succinate containing medium with a concentration of 25-50 wt. %. For further properties of this medium reference is made to what is stated above for the magnesium succinate containing medium to be provided to the second acidification reactor. Evaporation at elevated temperature at a pressure which is such that precipitation of magnesium succinate is prevented may be preferred for reasons of process control.

It may be particularly preferred for the embodiments in the two preceding paragraphs to be combined. In that case, a single magnesium succinate solution can be used as starting material for both evaporation steps. This embodiment is illustrated in FIG. 2, without being limited thereto or thereby.

In FIG. 2, an aqueous magnesium succinate solution with a concentration of 5-15 wt. % is provided through line (8). It is split into a feed line (9) to a first evaporation reactor (10) and a feed line (11) into a second evaporation reactor (12). In first evaporation reactor (10), water is evaporated and removed through line (13), in such an amount that an aqueous magnesium succinate containing medium is obtained with a magnesium succinate concentration in the range of 18-23 wt. %. The magnesium succinate containing medium is withdrawn through line (1), and provided to a first acidification reactor (2), as discussed above for FIG. 1. In second evaporation reactor (12), water is evaporated and removed through line (14), in such an amount that an aqueous magnesium succinate containing medium is obtained with a magnesium succinate concentration in the range of 25-50 wt. %. The magnesium succinate containing medium is withdrawn through line (5), and provided to the second acidification reactor (6), as discussed above for FIG. 1. For the further elements of FIG. 2, reference is made to what is stated above for the corresponding elements in FIG. 1.

The present invention thus also pertains to a process comprising the steps of
   subjecting a magnesium succinate solution with a magnesium succinate concentration of 5-15 wt. % to at least one concentration step in at least one evaporation reactor, to obtain a first magnesium succinate containing medium with a magnesium succinate concentration of 18-23 wt. % and a second magnesium succinate containing medium with a concentration of 25-50 wt. %,
   providing the first magnesium succinate containing medium with a magnesium succinate concentration of 18-23 wt. % to a first acidification reactor where it is contacted with hydrogen chloride to form a solution of succinic acid, magnesium chloride and hydrogen chloride,
   contacting the second magnesium succinate containing medium with a magnesium succinate concentration of 25-50 wt. % in a second acidification reactor with the solution of succinic acid, magnesium chloride and hydrogen chloride withdrawn from the first acidification reactor, to form an aqueous mixture comprising magnesium chloride and succinic acid with a succinic acid concentration of at least 18 wt. %.

In FIG. 2, two separate evaporators are presented. As will be evident to the skilled person it is also possible to carry out the evaporation step to generate the first magnesium succinate containing medium and the evaporation step to generate the second magnesium succinate containing medium in a single evaporation unit by passing the solution though the unit in a larger or smaller number of cycles.

The aqueous mixture comprising magnesium chloride and succinic acid derived from the second acidification reactor can be processed as desired. In one embodiment, it is provided to a precipitation/separation step, where succinic acid is precipitated from the solution, resulting in the formation of succinic acid in solid form, which can be separated from the magnesium chloride solution.

As indicated above, the aqueous mixture comprising magnesium chloride and succinic acid derived from the second acidification reactor may already comprise succinic acid in solid form. To increase the amount of succinic acid present in solid form, measures conventional in the art may be employed. Measures include decreasing the temperature of the mixture, removal of water to increase the succinic acid concentration, and adding an antisolvent. The latter embodiment may be less preferred because it encompasses the addition of further components to the system.

In this context it should be noted that the method according to the invention makes it possible to obtain a product mixture with a higher succinic acid concentration and a higher magnesium chloride concentration than the single step method described in WO2013/025105. As a higher succinic acid concentration and a higher magnesium chloride concentration both result in an increased precipitation of succinic acid, the succinic acid yield is improved. This also has the advantage that the remaining magnesium chloride solution contains less succinic acid, which is advantageous in the further processing of that solution.

For further information on the precipitation of succinic acid from the magnesium chloride solution, reference is made to WO2013/025105.

The precipitated succinic acid can be separated from the magnesium chloride solution by methods known in the art. Suitable methods include filtration techniques, also including membrane filtration, sedimentation techniques, techniques based on gravity separation such as decantation, and techniques comprising a centrifugation step. Combinations of various methods, e.g. centrifugation followed by decantation can also be used.

The magnesium chloride solution resulting from the separation step may be processed as desired. In one embodiment, if there are still significant amounts of succinic acid remaining in the magnesium chloride solution, further precipitation steps can be carried out, followed by further separation steps.

In one embodiment the magnesium chloride solution, whether or not after having been subjected to further precipitation/separation steps can be provided to a thermal decomposition step. In a thermal decomposition step, magnesium chloride is decomposed at a temperature of at least 300° C., in particular in the range of 350 to 600° C. in the presence of water to form magnesium oxide in solid form, and hydrogen chloride in gaseous form. Suitable thermal decomposition methods are known in the art and require no further elucidation here. They are, e.g., described in WO 2013/025105, WO 2015/00956, and non-prepublished PCT application PCT/EP2015/056895.

In one embodiment the starting solution of magnesium succinate with a magnesium succinate concentration of 5-15 wt. % is derived from a fermentation process. In such a fermentation process, a carbon source is fermented in a fermentation medium by means of a microorganism capable of producing succinic acid to form succinic acid, and neutralizing at least part of the succinic acid with a magnesium base selected from magnesium oxide, magnesium hydroxide, magnesium carbonate, and magnesium bicarbonate. Once the fermentation has been completed, the fermentation medium comprising dissolved magnesium succinate will generally be submitted to a biomass removal step, by methods known in the art. The resulting magnesium succinate solution can be provided as starting material in the process according to the invention, in particular as feed to the first and second evaporation steps described above. Fermentation processes are known in the art, and require no further elucidation here.

In one embodiment, where the process according to the invention comprises a thermal decomposition step, the magnesium oxide generated in the thermal decomposition step is provided as neutralizing agent to a fermentation process generating succinic acid, either directly, or after conversion into magnesium hydroxide, magnesium carbonate, or magnesium bicarbonate.

In one embodiment, where the process according to the invention comprises a thermal decomposition step, the hydrogen chloride generated in the thermal decomposition step is provided to the first acidification reactor, in gaseous form or after dissolution or absorption in water to form an aqueous HCl solution. It is a preferred embodiment of the present invention for the HCl generated in the thermal decomposition step to be provided to the first acidification reactor in gaseous form.

A preferred embodiment of the present invention is illustrated in FIG. 3.

In FIG. 3, an aqueous mixture comprising magnesium chloride and succinic acid with a succinic acid concentration of at least 18 wt. % is withdrawn through line (7), and provided to a separation step (15). In separation step (15) succinic acid is separated off, and withdrawn through line (16). A magnesium chloride solution is withdrawn through line (17), and provided to a thermal decomposition step (18), where the magnesium chloride is decomposed to form magnesium oxide, withdrawn through line (19) and HCl. The HCl is withdrawn from the thermal decomposition step through line (3) and provided to the first acidification reactor (2), either, and preferred, in the gaseous form in which it is obtained in the thermal decomposition step, or after absorption into water to form an aqueous medium (in absorption apparatus not shown). For a description of the further elements in FIG. 3, reference is made to the description of FIGS. 1 and 2.

In one embodiment the present invention pertains to an integrated process comprising the steps of
subjecting a carbon source to a fermentation step to form succinic acid, which fermentation step comprises the steps of fermenting a carbon source by means of a micro-organism capable of producing succinic acid in a fermentation broth to form succinic acid and neutralizing at least part of the succinic acid by adding a magnesium base selected from magnesium oxide, magnesium hydroxide, magnesium carbonate, and magnesium bicarbonate, thereby obtaining a magnesium succinate solution with a magnesium succinate concentration of 5-15 wt. %,
subjecting a magnesium succinate solution with a magnesium succinate concentration of 5-15 wt. % to at least one concentration step in at least one evaporation reactor, to obtain a first magnesium succinate containing medium with a magnesium succinate concentration of 18-23 wt. % and a second magnesium succinate containing medium with a concentration of 25-50 wt. %,
providing the first magnesium succinate containing medium with a magnesium succinate concentration of 18-23 wt. % to a first acidification reactor where it is contacted with hydrogen chloride to form a solution of succinic acid, magnesium chloride and hydrogen chloride,
contacting the second magnesium succinate containing medium with a magnesium succinate concentration of 25-50 wt. % in a second acidification reactor with the solution of succinic acid, magnesium chloride and hydrogen chloride withdrawn from the first acidification reactor, to form an aqueous mixture comprising magnesium chloride and succinic acid with a succinic acid concentration of at least 18 wt. %,
subjecting the aqueous mixture of magnesium chloride and succinic acid with a succinic acid concentration of at least 18 wt. % to a precipitation step and a separation step, to generate solid succinic acid and a magnesium chloride solution,
providing the magnesium chloride solution to a thermal decomposition step at a temperature of at least 300° C., resulting in the formation of magnesium oxide and hydrogen chloride,
optionally providing the magnesium oxide as neutralising agent to the fermentation step, as such or after conversion to magnesium hydroxide, magnesium carbonate, or magnesium bicarbonate,
providing the hydrogen chloride to the first acidification reactor, either directly, or after absorption in water to form a hydrogen chloride solution.

The various steps of the process according to this embodiment of the invention may be carried out as described in more detail above.

It will be evident to the skilled person that the various aspects of the present invention which are described above in different paragraphs may be combined, unless they are mutually exclusive.

The invention and certain embodiments of the inventions are illustrated by the following examples and/or embodiments, without being limited thereto or thereby.

COMPARATIVE EXAMPLE

In this example, reference is made to the process as described in WO 2013/025105 A1. FIG. 4 describes the set up for the process that has been used in this comparative example.

An aqueous magnesium succinate solution with a concentration of 7 wt. % and a temperature of 80° C. is provided through feed line (9) to a evaporation reactor (10) where water is evaporated and removed through line (13) in such an amount that an aqueous magnesium succinate solution (1) is obtained with a magnesium succinate concentration in the range of 22 wt. %, with a temperature of 95° C. The magnesium succinate solution (1) is provided to an acidification reactor (2). In the acidification reactor, HCl is added through line (3) in gaseous form, at a temperature of 115° C. This results in the formation of an aqueous solution (4) comprising magnesium chloride and succinic acid with a succinic acid concentration of 18 wt. %, and a magnesium chloride concentration of 15 wt. %, the solution having a temperature of 95° C. This aqueous solution is subjected to a precipitation step and a separation step, to generate solid succinic acid and a magnesium chloride solution. The overall yield of succinic acid is 95 wt. %.

EXAMPLE

In this example, reference is made to the process as illustrated in FIG. 2.

An aqueous magnesium succinate solution with a concentration of 7 wt. % and a temperature of 80° C. is provided through line (8). It is split into a feed line (9) to a first evaporation reactor (10) and a feed line (11) into a second evaporation reactor (12).

In first evaporation reactor (10), water is evaporated and removed through line (13), in such an amount that an aqueous magnesium succinate solution is obtained with a magnesium succinate concentration in the range of 22 wt. %, with a temperature of 95° C. The magnesium succinate solution is withdrawn through line (1), and provided to a first acidification reactor (2). In second evaporation reactor (12), water is evaporated and removed through line (14), in such an amount that an aqueous magnesium succinate solution is obtained with a magnesium succinate concentration in the range of 35 wt. %. The magnesium succinate solution has a temperature of 115° C. and is at autogenous pressure. It is withdrawn through line (5), and provided to the second acidification reactor (6).

In the first acidification reactor (2), HCl is added through line (3) in gaseous form, at a temperature of 115° C., and an aqueous solution with a temperature of 95° C. comprising succinic acid in a concentration of 15 wt. %, magnesium chloride in a concentration of 18 wt. %, and HCl is withdrawn through line (4), and provided to second acidification reactor (6). In second acidification reactor (6), it is combined with the second magnesium succinate containing medium. This results in the formation of an aqueous solution comprising magnesium chloride and succinic acid with a succinic acid concentration of 21 wt. %, and a magnesium chloride concentration of 18 wt. %, the solution having a temperature of 120° C., which is withdrawn through line (7). This aqueous solution is subjected to a precipitation step and a separation step, to generate solid succinic acid and a magnesium chloride solution. The overall yield of succinic acid is larger than 97 wt. %.

The invention claimed is:

1. A method for providing a succinic acid solution, comprising the steps of:
   contacting a first magnesium succinate containing medium with a magnesium succinate concentration of 18-23 wt. % in a first acidification reactor with hydrogen chloride to form a solution of succinic acid, magnesium chloride, and hydrogen chloride, and
   contacting a second magnesium succinate containing medium with a magnesium succinate concentration of 25-50 wt. % in a second acidification reactor with the solution of succinic acid, magnesium chloride, and hydrogen chloride withdrawn from the first acidification reactor, to form an aqueous mixture comprising magnesium chloride and succinic acid with a succinic acid concentration of at least 18 wt. %.

2. The method of claim 1, wherein the first magnesium succinate containing medium and/or the second magnesium succinate containing medium are obtained by subjecting an aqueous magnesium succinate solution with a magnesium succinate concentration in the range of 5-15 wt. % to a concentration step in an evaporation reactor wherein water is evaporated to obtain a magnesium chloride solution with the specified concentration.

3. The method of claim 2, comprising the steps of:
   subjecting a magnesium succinate solution with a magnesium succinate concentration of 5-13 wt. % to at least one concentration step in at least one evaporation reactor, to obtain a first magnesium succinate containing medium with a magnesium succinate concentration of 18-23 wt. % and a second magnesium succinate containing medium with a concentration of 25-50 wt. %,
   contacting the first magnesium succinate containing medium with a magnesium succinate concentration of 18-23 wt. % in a first acidification reactor with hydrogen chloride to form a solution of succinic acid, magnesium chloride, and hydrogen chloride, and
   contacting the second magnesium succinate containing medium with a magnesium succinate concentration of 25-50 wt. % in a second acidification reactor with the solution of succinic acid, magnesium chloride, and hydrogen chloride withdrawn from the first acidification reactor, to form an aqueous mixture comprising magnesium chloride and succinic acid with a succinic acid concentration of at least 20 wt. %.

4. The method of claim 1, wherein the HCl provided to the first acidification reactor is provided in gaseous form.

5. The method of claim 1, wherein the HCl provided to the first acidification step is derived from the thermal decomposition of magnesium chloride.

6. The method of claim 1, which further comprises the steps of:
   subjecting the aqueous mixture comprising magnesium chloride and succinic acid with a succinic acid concentration of at least 18 wt. % to a precipitation step and a separation step, to generate solid succinic acid and a magnesium chloride solution,
   providing the magnesium chloride solution to a thermal decomposition step at a temperature of at least 300° C., resulting in the formation of magnesium oxide and hydrogen chloride, and
   providing the hydrogen chloride to the first acidification reactor, either directly in gaseous form, or after absorption into water to form a hydrogen chloride solution.

7. The method of claim 1, comprising the steps of:
   subjecting a carbon source to a fermentation step to form succinic acid, which fermentation step comprises the steps of fermenting a carbon source with a microorganism capable of producing succinic acid in a fermentation broth to form succinic acid and neutralizing at least part of the succinic acid by adding a magnesium base selected from magnesium oxide, magnesium hydroxide, magnesium carbonate, and magnesium bicarbonate, thereby obtaining a magnesium succinate solution with a magnesium succinate concentration of 5-15 wt. %,
   subjecting the magnesium succinate solution with a magnesium succinate concentration of 5-15 wt. % to at least one concentration step in at least one evaporation reactor, to obtain the first magnesium succinate containing medium with a magnesium succinate concentration of 18-23 wt. % and the second magnesium succinate containing medium with a concentration of 25-50 wt. %,
   contacting the first magnesium succinate containing medium with a magnesium succinate concentration of 18-23 wt. % in a first acidification reactor with hydrogen chloride to form a solution of succinic acid, magnesium chloride, and hydrogen chloride,
   contacting the second magnesium succinate containing medium with a magnesium succinate concentration of 25-50 wt. % in a second acidification reactor with the solution of succinic acid, magnesium chloride, and hydrogen chloride withdrawn from the first acidification reactor, to form the aqueous mixture comprising magnesium chloride and succinic acid with a succinic acid concentration of at least 18 wt. %,
   subjecting the aqueous mixture comprising magnesium chloride and succinic acid with a succinic acid concentration of at least 18 wt. % to a precipitation step and a separation step, to generate solid succinic acid and a magnesium chloride solution,
   providing the magnesium chloride solution to a thermal decomposition step at a temperature of at least 300° C., resulting in the formation of magnesium oxide and hydrogen chloride,
   optionally providing the magnesium oxide as neutralising agent to the fermentation step, or after conversion to magnesium hydroxide, magnesium carbonate, or magnesium bicarbonate, and
   providing the hydrogen chloride to the first acidification reactor, either directly, or after dissolution in water to form a hydrogen chloride solution.

8. The method of claim 2, wherein both the first magnesium succinate containing medium and the second magnesium succinate containing medium are obtained by subjecting an aqueous magnesium succinate solution with a magnesium succinate concentration in the range of 5-15 wt. % to a concentration step in an evaporation reactor wherein water is evaporated to obtain a magnesium chloride solution with the specified concentration.

9. A process for the production of butanediol, comprising:
   preparing solid succinic acid by the method of claim 6,
   converting the solid succinic acid to a succinic acid ester, and
   converting the succinic acid ester to the butanediol.

10. A process for the production of butanediol, comprising:
   preparing solid succinic acid by the method of claim 7,
   converting the solid succinic acid to a succinic acid ester, and
   converting the succinic acid ester to the butanediol.

* * * * *